United States Patent [19]

Allenmark et al.

[11] Patent Number: 4,790,978
[45] Date of Patent: Dec. 13, 1988

[54] METHOD FOR DISINFECTION

[75] Inventors: Stig Allenmark, Kullavik; Magnus Lindstedt; Lars Edebo, both of Göteborg, all of Sweden

[73] Assignee: Berol Kemi AG, Stenungsund, Sweden

[21] Appl. No.: 948,261

[22] Filed: Dec. 31, 1986

[30] Foreign Application Priority Data

Jan. 7, 1986 [SE] Sweden .................. 8600046

[51] Int. Cl.⁴ .................................. A61L 2/18
[52] U.S. Cl. .................................. 422/28; 426/326; 426/335; 210/764; 514/556; 514/642
[58] Field of Search .................. 422/28; 426/326, 335; 210/764; 514/556, 642

[56] References Cited

U.S. PATENT DOCUMENTS

| | | | |
|---|---|---|---|
| 4,446,103 | 5/1984 | Nudel et al. | 422/28 |
| 4,499,077 | 2/1985 | Stockel et al. | 514/642 |
| 4,525,346 | 6/1985 | Stark | 514/642 |
| 4,601,954 | 7/1986 | Coleman | 422/28 |

FOREIGN PATENT DOCUMENTS 1061457  3/1967  United Kingdom .

OTHER PUBLICATIONS

I Métayer, Ann Pharm. Franc. 10, pp. 435-439, 1952.
T. Nakamiya et al., Antibacterial Activity of Lauryl Ester of DL-Lysine, Ferment Technology, vol. 54, No. 6, pp. 36-374, 1976.
A. E. Epsbtein et al., Bactericidial Quaternary Ammonium Salts Derived from Monochloro Acetate Esters, Khim. Farm. Zh. 14, 23 (1980), pp. 292-295.

Primary Examiner—Barry S. Richman
Assistant Examiner—Jill Johnston
Attorney, Agent, or Firm—Spencer & Frank

[57] ABSTRACT

Use of a long chain alkyl ester as a temporary microbicide at pH-values from about 6 to about 8.5. The long-chain alkyl ester has the formula

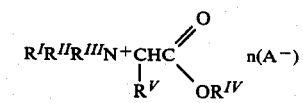

where $R^I$, $R^{II}$, and $R^{III}$ are hydrogen or lower alkyl groups and $R^{IV}$ is an long chain alkyl group having 10-18 carbon atoms, $R^V$ is hydrogen or a group having the formula $R^{VI}N^+H_3$ where $R^{VI}$ is an alkylene group having 3-4 carbon atoms, A is a monovalent counter ion and n is the number of cationic groups in the ester compound. The ester exhibits a temporary microbicidal effect due to a hydrolytic reaction. As a consequence the toxic effect on human and animals cells and tissues will be low.

14 Claims, No Drawings

METHOD FOR DISINFECTION

BACKGROUND OF THE INVENTION

Amphiphilic compounds of the quaternary ammonium type have for a long time been known to exhibit strong antimicrobial activity, the disclosure by Domagk in 1935 having great impact on the development of this field. (G. Domagk, Dtsch. Med. Wochenschr. 61, 829 (1935)). It has become evident, however, from studies of acute as well as chronic toxicity, that these compounds may give rise to skin irritation and hypersensitivity, and therefore are not quite recommendable for certain applications.

SUMMARY OF THE INVENTION

Therefore, it is an object of this invention to find antimicrobial compounds which do not have the drawback mentioned above. Another object of the invention is to permit a rapid inactivation by a controllable degradation of the antimicrobial compound. Still another object is that the degradation will take place at pH-values from about 6 to about 8.5 which is a pH-value that does not give rise to skin irritation and the like.

It has now been foiund that these objects are met by using a long chain alkyl ester having the general formula

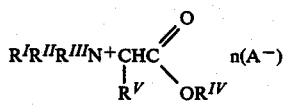

I where $R^I$, $R^{II}$, and $R^{III}$ are hydrogen or lower alkyl groups and $R^{IV}$ is an long chain alkyl group having 10–18 carbon atoms, $R^V$ is hydrogen or a group having the formula $R^{VI}N^+H_3$ where $R^{VI}$ is an alkylene group having 3–4 carbon atoms, A is a monovalent counter ion and n is the number of cationic groups in the ester compound, as a temporary microbicide in an aqueous medium at a pH-vlue from about 6 to about 8.5 for disinfection of products or in products for disinfection to be brought in contact with food, human beings and animals, e.g. human and animal cells and tissue. In the present invention the microorganisms are inactivated in an initial phase by exposing the microorganisms in an aqueous medium at a pH-value from about 6 to about 8.5 to the long-chain alkyl ester and the long-chain alkyl ester is detoxicated due to a hydrolytic reactiion which takes place concurrently and subsequently with the inactivation of the microorganisms so that the content of the ester in a short time reaches an innocuous level. The lower alkyl groups $R^I$, $R^{II}$ and $R^{III}$ are preferably alkyl groups having 1–4 carbon atoms and most preferably they are methyl groups. Preferably $R^{IV}$ is a straight chain alkyl group. The counter ion A is normally a halide ion, such as chloride, or $HSO_4^-$. Examples of preferred embodiments are esters having the formulae

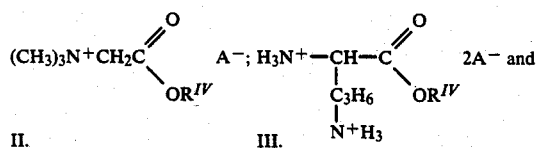

II.  III.

-continued

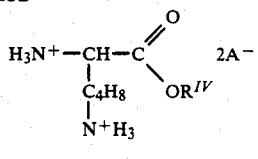

IV.

where $R^{IV}$ and A have the above meanings.

In general, ordinary alkyl ester compounds have an extremely slow hydrolysis rate at these pH-values. The charged long chain alkyl esters I exhibit a useful rate of ester hydrolysis in a pH-range from about 6 to about 8.5 and especially in the pH-range from about 7 to about 8 which, in the present invention, is advantageously used in order to obtain an initially complete microbicidal effect while only a limited toxic effect is exerted against human beings and animals. The latter advantage will be more pronounced when longer contact times, e.g. half an hour or more, are had between the disinfected or disinfecting products and human beings and animals. Normally the long-chain alkyl esters are added in such an amount that the effective concentration in the aqueous medium will be at least 2 ppm, preferably between 5 and 200 ppm, even if other concentrations may be used depending on the specific conditions at application.

Examples of lower alkyl groups in the above formula are methyl, ethyl, propyl, isopropyl, butyl, sec. butyl, and isobutyl, but ethyl and especially methyl are the preferred groups. The long chain alkyl group $R^{IV}$ can be decanyl, dodecanyl, dodecenyl, tetradecanyl, hexadecanyl, octadecanyl, octadecenyl, octadecandienyl, and octadecantrietnyl, and of these groups especially the saturated groups are preferred.

Compounds having the above formula have earlier been disclosed in the chemical literature (I. Métayer, Ann pharm. franc. 10, 435, 439 (1952)) and they have also been found to have antibacterial effects (A. E. Epstein et al., Khim. Farm. Zh. 14, 23 (1980) and Teruaki Nakamiya et al., Ferment. Technol. Vol. 54, No 6, p 369–374, 1976). No reports referring to the loss of biological activity as a result of ester hydrolysis in the pH-region around 7 have been made, and therefore said literature does not indicate any advantages to use these compounds instead of prior known microbicidal compounds.

The main idea behind this invention originates from the fact that, at appropriate concentration levels, the time needed for full antimicrobial effect is generally fairly short. In most practical situations the antimicrobial agent is also administered in a very large excess. Therefore, in many applications the toxic compound is active for a long time after it has exerted its antimicrobial action which is both undesirable and unnecessary. The invention discloses a principle, according to which the antimicrobial compound loses its biological activity and toxic action by a hydrolytic reaction. The rate of hydrolysis can be regulated by small changes of pH and electrolyte concentration leading to harmless end-products within the physiologically suitable pH-range from about 6 to about 8.5.

The solubility of the esters in polar organic solvents, such as lower alcohols and alcohol/water mixtures, is of the order 1 g/ml. Such formulations are highly stable and allow long-term storage.

The esters are highly active against a brod spectrum of Grampositive and Gramnegative bacteria, as well as fungi, and examples of test data are given below.

The temporary disinfecting effect of the esters may be used in hygienic products such as diapers, tampons, masks, napkins, and cosmetic powders. It may also be employed in disinfectants, e.g. for food industry equipment, in bubble baths, swimming pools, and mouthwashes; and for treatment of packages, food industry equipment, food, drinking water etc. The esters can be applied to webs and garments by dipping or spraying a slightly acid, aqueous solution of the esters followed by a rapid drying. Cellulosic fibers may be impregnated by adding the esters to the cellulose pulp slurry in a headbox. When used in dry form, the esters may have the form of a powder or a tablet, for example, an effervescant tablet.

The esters II may be prepared by conventional method by a reacting a chloro- or bromoacetyl halide with an alcohol in a halogenated hydrocarbon to an alkyl chloro- or bromoacetate. This ester is then converted into an ester having the formula II by a reaction with gaseous trialkylamine in a solvent such as acetone or toluene. The esters III and IV may be manufactured by direct esterification of the corresponding amino acids with a long chain fatty alcohol using p-toluenesulphonic acid as a catalyst.

DESCRIPTION OF THE PREFERRED EMBODIMENTS

The following examples will further illustrate the invention.

Example 1

The bactericidal effect of three esters having the following formula

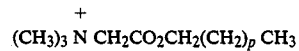
$(CH_3)_3 \overset{+}{N} CH_2CO_2CH_2(CH_2)_p CH_3$ where p was 10, 12 and 14, respectively, were determined and compared with cetyltrimethylammonium bromide (CTAB), a wellknown bactericide. The effect was measured as the concentration needed for reducing the number of viable bacteria by a factor of $10^5$ using $E.$ $coli$ (NCTC 10418) as test organism during 5 minutes contact time. The results are shown in the Table below.

TABLE 1

| Compound p | Concentration ppm |
|---|---|
| 10 | 50 |
| 12 | 12.5 |
| 14 | >100 |
| CTAB | 12.5 |

From the result it is evident that the esters have an appropriate bactericidal effect.

Example 2

The activity towards a series of microorganisms was determined for the compound in Example 1 having a total of 14 carbon atoms in its alkyl chain, i.e., p=12, a betaine ester. Relevant test data are given in the Table below. The activity is expressed as log (cfu/ml) at a 12.5 ppm level and a 5 min contact time in phosphate buffered saline at room temperature. Effects are related to a control (without bactericide) and to CTAB. G+ and G− denote Grampositive and Gramnegative species, respectively.

TABLE 2

| Microorganisms (Type) | log (cfu/ml) | | |
|---|---|---|---|
| | control | betaine ester | CTAB |
| Bacillus megaterium (G+) | 6.7 | <3.3 | <3.3 |
| E. coli (G−) | 7.0 | <3.3 | <3.3 |
| Candida albicans (yeast) | 6.2 | 6.2 | 5.7 |
| Pseudomonas aeruginosa (G−) | 7.4 | 7.5 | 7.5 |
| Staphylococcus aureus (G+) | 5.8 | <3.3 | <3.3 |
| Salmonella typhimurium (G−) | 5.5 | 3.9 | 3.8 |

The effects of the betaine ester and of CTAB are the same within experimental error. Except against the more resistant Ps. aeruginosa and the yeast C. albicans, high activities are found even at these low concentrations.

Example 3

The rate of alkaline hydrolysis of the present esters of betaines was determined for the compound in Example 1 having a total of 14 carbon atoms in its alkyl chain (p=12). The conditions during the test and results obtained are given in the Table below.

TABLE 3

Hydrolysis (given in %) at various pH-values and reaction times at 30° C.:

| time hrs | pH | | | | | | | |
|---|---|---|---|---|---|---|---|---|
| | 2.6 | 3 | 4 | 5 | 6 | 7 | 8 | 9 |
| 0.25 | | | | | | | | 96 |
| 0.5 | | | | | | | 12 | 100 |
| 1 | | | | | | 5 | 60 | 100 |
| 1.5 | | | | | | | 87 | |
| 2 | | | | | | 2 | 10 | |
| 3 | | | | | | | 100 | |
| 4 | | | | | | | 37 | 100 |
| 8 | <1 | <1 | 1 | | | | 80 | |
| 18 | | | | | | 16 | | |
| 20 | | | | | | | 98 | |
| 24 | <1 | 2 | 3 | 5 | | | | |
| 46 | | | | | | 85 | | |
| 48 | <1 | 2 | 5 | 10 | | | | |
| 120 | | | | | | | | |
| 144 | 1 | 6 | 12 | 22 | | | | |

The rate of hydrolysis is also determined dependent. On a temperature increase from 25° C. to 30° C., the half-life at pH 7.0 is decreased from 9 to 5 hrs.

Example 4

The rate of hydrolysis and thereby the duration of the biological activity of the esters can also be regulated according to this invention by the salt concentration of the medium. The rate of hydrolysis is decreased considerably by an increase in sodium chloride concentration. In the Table below, the effect of sodium chloride on hydrolysis of the compound in Example 2 at pH 7.9 and 30° C. is shown.

TABLE 4

| t, hrs | Hydrolysis, % | | | |
|---|---|---|---|---|
| | Molarity of NaCl | | | |
| | 0 | 0.1 | 0.5 | 1.0 |
| 1 | 51 | 9 | 6 | 2 |
| 2 | 95 | 56 | 9 | 4 |
| 5 | 100 | 100 | 28 | 12 |
| 48 | | | 95 | 77 |

Example 5

A solution of 150 ppm of the compound in Example 1 in 10 mM phosphate buffer, pH 8.0, was analyzed at different points of time with respect to degree of hydrolysis, as well as bactericidal effect against *E. coli* (NCTC 10418). The degree of hydrolysis was determined by analysis of the liberated 1-tetradekanol by gas chromatography (packed 4 ft glass column with 3% SP-2100 on 80/100 Supelcoport; isotermally at 130° C.). The 1-tetradekanol was isolated by careful extraction with hexane. Internal standardization was carried out by means of 1-hexadecanol. Bactericidal effect was determined by dilution of a 1 ml sample to 25 ppm with 5 ml of a sterile buffer followed by addition of 60 μl of the bacterial suspension. After 5 min at room temperature, a 100-fold dilution and spreading on an agar plate using a Spiral Plater system was performed. The plates were incubated at 37° C. for 20 hrs and counted. Data from the experiments are given in the Table below.

TABLE 5

Hydrolysis and the effect on the bacterial activity.

| Time, min | Hydrolysis, % | Viable counts, cfu/ml (control: 7.1 × 10$^6$) |
|---|---|---|
| 5 | | 0 |
| 23 | 3 | |
| 30 | | 4.1 × 10$^3$ |
| 64 | 25 | |
| 109 | | 3.0 × 10$^6$ |
| 118 | 55 | |
| 149 | 86 | |
| 158 | | 7.9 × 10$^6$ |
| 179 | 89 | |
| 199 | | 7.8 × 10$^6$ |
| 217 | 100 | |
| 238 | 100 | |

Example 6

The compounds listed below were tested at a 25 ppm level against five different microorganisms in a buffered water solution (10 mM, pH 7.4). One set of solutions was immediately inoculated while the other set was kept at 30° C. for 24 hrs prior to inoculation. The contact time was 5 min.

The results shown in Table 6 were obtained.

TABLE 6

| Compound | Microorganism | Δ log 0 hrs | cfu/ml 24 hrs |
|---|---|---|---|
| LE 16 | E.c. | 4.3 | 3.2 |
| | C.a. | 6.1 | 0.7 |
| ORN 14 | E.c. | 7.1 | 0 |
| | St.a. | 5.2 | 0 |
| | S.t. | 6.7 | 0 |
| | Ps.a. | 8.2 | <3.2 |
| | C.a. | 6.1 | 0 |
| BE 14 | E.c. | 7.1 | 0.2 |
| | St.a. | 6.5 | 0.2 |
| | S.t. | 6.7 | 0.1 |
| | Ps.a. | 8.2 | <3.2 |
| | C.a. | 3.3 | 0 |
| CTAB | E.c. | 7.1 | 7.1 |
| | St.a. | 6.5 | 6.4 |
| | S.t. | 6.7 | 6.5 |
| | Ps.a. | 8.2 | 8.2 |
| | C.a. | 6.1 | 6.0 |

$$\text{LE 16} = \text{N}^+\text{H}_3-\underset{\underset{\text{N}^+\text{H}_3}{|}}{\overset{\overset{\text{C}_4\text{H}_8}{|}}{\text{CHC}}}\begin{matrix}\diagup\!\!\!\diagup\text{O}\\\diagdown\text{OC}_{16}\text{H}_{33}\end{matrix}\quad 2\text{Cl}^-$$

$$\text{ORN 14} = \text{N}^+\text{H}_3-\underset{\underset{\text{N}^+\text{H}_3}{|}}{\overset{\overset{\text{C}_3\text{H}_6}{|}}{\text{CHC}}}\begin{matrix}\diagup\!\!\!\diagup\text{O}\\\diagdown\text{OC}_{14}\text{H}_{29}\end{matrix}\quad 2\text{Cl}^-$$

$$\text{BE 14} = (\text{CH}_3)_3\text{N}^+-\text{CH}_2-\text{C}\begin{matrix}\diagup\!\!\!\diagup\text{O}\\\diagdown\text{OC}_{14}\text{H}_{29}\end{matrix}\quad \text{Cl}^-$$

E.c. = *E. coli* NCTC 10418
St.a. = *Staphylococcus aureus* NCTC 10788
S.t. = *Salmonella typhimurium*
Ps.a. = *Pseudomonas aeruginosa* ATCC 15442
C.a. = *Candica albicans* ATCC 10231

From the results it is evident that the antimicrobial effects of the different long-chain alkyl esters were of the same magnitude as the effect of cetyltrimetylammonium bromide. After 24 hours in the aqueous solution, the effects diminished considerably for the microbicides of the invention. The esters designated with ORN and BE 14 exhibit especially favourable proerties.

Example 7

Lysine-tetradecylester, betaine-tetradecylester, and betaine-hexadecylester were tested at different concentrations for the disinfection of drinking water. The drinking water contained *Salmonella typhimurium* 395 MS AND *Shigella sonnei*. At a concentration of 10 ppm of the microbicide at a pH of about 7 the above mentioned bacteria were completely inactivated within 10 minutes. Complete inactivation means that more than 99.99% of the bacteria were killed. In the presence of contaminating material (0.2% bovine serum albumin) concentrations of 100 ppm were sufficient to cause complete inactivation in 10 minutes. Also *Camphylobacter jejuni* was inactivated to the same extent under these conditions.

Example 8

Disinfection of water containing *Pseudomonas aeruginosa* strain 10783 was carried out by adding betaine-tetradecylester and lysine-tetradecylester. The species *Pseudomonas aeruginosa* is well known for its resistance against cationic surfactant disinfectants. At a concentration of the esters of 100 ppm the bacteria were completely inactivated within one minute. The same results were also obtained in the presence of contaminating organic material (0.2% bovine serum albumin).

We claim:

1. A process of disinfecting at least one of food, human beings, animals and products to be brought in contact with one of food, human beings, and animals to combat microorganisms, comprising:
   exposing the at least one of food, human beings, animals and products to a freshly prepared composition having a pH-value ranging from about 6 to about 8.5 and being comprised of an aqueous medium and a long-chain alkyl ester compound having the formula:

$$R^{I}R^{II}R^{III}N^{+}\underset{R^{V}}{\overset{|}{C}}HC\overset{O}{\underset{OR^{IV}}{\diagup\!\!\!\diagdown}} \quad n(A^{-})$$

where $R^{I}$, $R^{II}$, AND $R^{III}$ are hydrogen or lower alkyl groups, $R^{IV}$ is a long-chain alkyl group having 10-18 carbon atoms, $R^{V}$ is hydrogen or a group having the formula $R^{VI}N^{+}H_3$, where $R^{VI}$ is an alkylene group having 3-4 carbon atoms, A is a monovalent counter ion and n is a number of cationic groups in the ester compound.

2. The process according to claim 1, wherein the ester compound has the general formula:

$$(CH)_3N^{+}CH_2C\overset{O}{\underset{OR^{IV}}{\diagup\!\!\!\diagdown}} \quad A^{-}.$$

3. The process according to claim 1, wherein the ester compound has the general formula:

$$H_3N^{+}\!\!-\!\!\underset{\underset{N^{+}H_3}{\overset{|}{C_3H_6}}}{\overset{|}{C}H}\!\!-\!\!C\overset{O}{\underset{OR^{IV}}{\diagup\!\!\!\diagdown}} \quad 2A^{-}.$$

4. The process according to claim 1, wherein the ester compound has the formula:

$$H_3N^{+}\!\!-\!\!\underset{\underset{N^{+}H_3}{\overset{|}{C_4H_8}}}{\overset{|}{C}H}\!\!-\!\!C\overset{O}{\underset{OR^{IV}}{\diagup\!\!\!\diagdown}} \quad 2A^{-}.$$

5. The process according to claim 1, wherein $R^{IV}$ is a straight chain alkyl group.

6. The process according to claim 1, where the microorganisms combatted are selected from bacteria and fungi.

7. The process according to claim 6, wherein the microorganisms combatted are bacteria and are selected from Gramnegative and Grampositive bacteria.

8. A process of disinfecting at least one of food, human beings, animals and products to be brought in contact with one of food, human beings and animals to combat microorganisms, comprising:

exposing the microorganisms to inactivate the microorganisms in an initial phase to a freshly prepared composition having a pH-value ranging from about 6 to about 8.5 and being comprised of an aqueous medium and a long-chain alkyl ester compound having the formula:

$$R^{I}R^{II}R^{III}N^{+}\underset{R^{V}}{\overset{|}{C}}HC\overset{O}{\underset{OR^{IV}}{\diagup\!\!\!\diagdown}} \quad n(A^{-})$$

where $R^{I}$, $R^{II}$, AND $R^{III}$ are hydrogen or lower alkyl groups, $R^{IV}$ is a long-chain alkyl group having 10-18 carbon atoms, $R^{V}$ is hydrogen or a group having the formula $R^{VI}N^{+}H_3$, where $R^{VI}$ is an alkylene group having 3-4 carbon atoms, A is a monovalent counter ion and n is a number of cationic groups in the ester compound, and detoxicating the long-chain alkyl ester compound of the composition due to hydrolytic reaction thereof which takes place concurrently with and subsequently to the initial phase and which reduces the ester compound content of the composition to innocuous levels.

9. The process according to claim 8, wherein the ester compound has the general formula:

$$(CH)_3N^{+}CH_2C\overset{O}{\underset{OR^{IV}}{\diagup\!\!\!\diagdown}} \quad A^{-}.$$

10. The process according to claim 8, wherein the ester compound has the general formula:

$$H_3N^{+}\!\!-\!\!\underset{\underset{N^{+}H_3}{\overset{|}{CH_3H_6}}}{\overset{|}{C}H}\!\!-\!\!C\overset{O}{\underset{OR^{IV}}{\diagup\!\!\!\diagdown}} \quad 2A^{-}.$$

11. The process according to claim 8, wherein the ester compound has the formula:

$$H_3N^{+}\!\!-\!\!\underset{\underset{N^{+}H_3}{\overset{|}{C_4H_8}}}{\overset{|}{C}H}\!\!-\!\!C\overset{O}{\underset{OR^{IV}}{\diagup\!\!\!\diagdown}} \quad 2A^{-}.$$

12. The process according to claim 8, wherein $R^{IV}$ is a straight chain alkyl group.

13. The process according to claim 8, where the microorganisms combatted are selected from bacteria and fungi.

14. The process according to claim 13, wherein the microorganisms combatted are bacteria and are selected from Gramnegative and Grampositive bacteria.

* * * * *

UNITED STATES PATENT AND TRADEMARK OFFICE
CERTIFICATE OF CORRECTION

PATENT NO. : 4,790,978
DATED : December 13th, 1988
INVENTOR(S) : Stig Allenmark, Magnus Lindstedt, Lars Edebo It is certified that error appears in the above-identified patent and that said Letters Patent is hereby corrected as shown below:

In the heading of the patent, [73], please change "Berol Kemi AG" to --Berol Kemi AB--.

Signed and Sealed this

Twenty-fifth Day of April, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,790,978
DATED : December 13th, 1988
INVENTOR(S) : Stig Allenmark et al.

It is certified that error appears in the above-identified patent and that said Letters Patent is hereby corrected as shown below:

Column 7, line 21:
In claim 2, change "$(CH)_3$" in the formula to $--(CH_3)_3--$.
Column 8, line 27:
In claim 9, change "$(CH)_3$" in the formula to $--(CH_3)_3--$.

Signed and Sealed this

Second Day of November, 1993

Attest:

BRUCE LEHMAN

Attesting Officer     Commissioner of Patents and Trademarks